United States Patent [19]
Meade

[11] Patent Number: 6,013,170
[45] Date of Patent: Jan. 11, 2000

[54] DETECTION OF ANALYTES USING REORGANIZATION ENERGY

[75] Inventor: Thomas J. Meade, Altadena, Calif.

[73] Assignee: Clinical Micro Sensors, Inc., Pasadena, Calif.

[21] Appl. No.: 09/096,504

[22] Filed: Jun. 12, 1998

Related U.S. Application Data

[63] Continuation of application No. 08/873,977, Jun. 12, 1997.

[51] Int. Cl.$^7$ .............................. C12Q 1/00; C12Q 1/70; C25B 11/00; G01N 27/26

[52] U.S. Cl. .................................. 205/777.5; 205/793.5; 205/778; 204/418; 204/415; 204/290; 204/403; 435/4; 435/5; 435/6; 435/7.1; 435/7.71; 435/7.72; 435/7.8; 435/7.9; 435/7.91; 435/7.93

[58] Field of Search .............................. 435/4, 5, 6, 7.1, 435/7.71, 7.72, 7.8, 7.9, 7.91, 7.93, 7.6, 7.4; 205/793.5, 777.5, 778; 204/418, 415, 290, 403

[56] References Cited

U.S. PATENT DOCUMENTS

| | | | |
|---|---|---|---|
| 4,707,352 | 11/1987 | Stavrianopoulos | 424/1.1 |
| 4,707,440 | 11/1987 | Stavrianopoulos | 435/6 |
| 4,711,955 | 12/1987 | Ward et al. | 536/29 |
| 4,840,893 | 6/1989 | Hill et al. | 435/6 |
| 5,013,831 | 5/1991 | Stavrianopoulos | 536/27 |
| 5,082,830 | 1/1992 | Brakel et al. | 514/44 |
| 5,175,269 | 12/1992 | Stavrianopoulos | 536/27 |
| 5,241,060 | 8/1993 | Englehardt et al. | 536/27 |
| 5,278,043 | 1/1994 | Bannwarth et al. | 536/23.1 |
| 5,312,527 | 5/1994 | Mikkelsen et al. | 204/153.12 |
| 5,328,824 | 7/1994 | Ward et al. | 435/6 |
| 5,403,451 | 4/1995 | Riviello et al. | 204/153.1 |
| 5,449,767 | 9/1995 | Ward et al. | 536/24.3 |
| 5,472,881 | 12/1995 | Beebe et al. | 436/94 |
| 5,476,928 | 12/1995 | Ward et al. | 536/24 |
| 5,565,552 | 10/1996 | Magda et al. | 534/11 |
| 5,573,906 | 11/1996 | Bannwarth et al. | 435/6 |
| 5,591,578 | 1/1997 | Meade et al. | 435/6 |
| 5,595,908 | 1/1997 | Fawcett et al. | 534/11 |
| 5,601,982 | 2/1997 | Sargent et al. | 435/6 |
| 5,620,850 | 4/1997 | Bamdad et al. | 530/300 |
| 5,705,348 | 1/1998 | Meade et al. | 435/6 |
| 5,770,369 | 6/1998 | Meade et al. | 435/6 |
| 5,780,234 | 7/1998 | Meade et al. | 435/6 |

FOREIGN PATENT DOCUMENTS

| | | |
|---|---|---|
| 2090904 | 9/1993 | Canada . |
| 0 63879 | 11/1982 | European Pat. Off. . |
| 0 234938 | 2/1987 | European Pat. Off. . |
| 0 229943 | 7/1987 | European Pat. Off. . |
| 0 599337 | 1/1994 | European Pat. Off. . |
| 0515615 | 9/1996 | European Pat. Off. . |
| 238166 | 2/1988 | Japan . |
| 6-41183 | 2/1994 | Japan . |
| 90/05732 | 5/1990 | WIPO . |
| 9 210 757 | 6/1992 | WIPO . |
| 93 10267 | 5/1993 | WIPO . |
| 93/23425 | 11/1993 | WIPO . |
| 9 515 971 | 6/1995 | WIPO . |
| 96 40712 | 12/1996 | WIPO . |
| 97/01646 | 1/1997 | WIPO . |
| 98/20162 | 5/1998 | WIPO . |

OTHER PUBLICATIONS

Alleman, K.S., et al., "Electrochemical Rectification at a Monolayer–Modified Electrode," *J. Phys. Chem.*, 100:17050–17058 (1996).

Arkin et al. "Evidence for Photoelectron Transfer Through DNA Intercalation," *J. Inorganic Biochem. Abstracts*, 6th International Conference on Bioinorganic Chemistry, 51(1) & (2):526 (1993).

Barisci et al., "Conducting Polymer Sensors," *TRIP*, 4(9):307–311 (1996).

Baum, R.M., "Views on Biological, Long–Range Electron Transfer Stir Debate," *C&EN*, pp. 20–23 (1993).

Bechtold, R., et al., "Ruthenium–Modified Horse Heart Cytochrome c: Effect of pH and Ligation on the Rate of Intramolecular Electron Transfer between Ruthenium(II) and Heme(III)," *J. Phys. Chem.*, 90(16):3800–3804 (1986).

Bidan, "Electroconducting conjugated polymers: new sensitive matrices to build up chemical or electrochemical sensors. A Review.," *Sensors and Actuators*, B6:45–56 (1992).

Biotechnology and Genetics: Genetic Screening Integrated Circuit, *The Economist* (Feb. 25–Mar. 3, 1995).

Boguslavsky, L. et al., "Applications of redox polymers in biosensors," *Solid State Ionics*, 60:189–197 (1993).

Bowler, B. E., et al., "Long–Range Electron Transfer in Donor (Spacer) Acceptor Molecules and Proteins," *Progress in Inorganic Chemistry: Bioinorganic Chemistry*, 38:259–322 (1990).

Brun, A. M., et al., "Photochemistry of Intercalated Quaternary Diazaaromatic Salts," *J. Am. Chem. Soc.*, 113:8153–8159 (1991).

Bumm, et al., "Are Single Molecular Wires Conducting?," *Science* 271:1705–1707 (1996).

Cantor, C.R. et al., "Report on the Sequencing by Hybridization Workshop," *Genomics*, 13:1378–1383 (1992).

Chang, I–Jy, et al., "High–Driving–Force Electron Transfer in Metalloproteins: Intramolecular Oxidation of Ferrocytochrome c by $Ru(2,2'-bpy)_2(im)(His-33)^{3+}$," *J. Am. Chem. Soc.*, 113:7056–7057 (1991).

Chidsey, C.E.D., et al., "Free Energy and Temperature Dependence of Electron Transfer at the Metal Electrolyte Interface," *Science*, 251:919–923 (1991).

Chidsey, et al., "Coadsorption of Ferrocene–Terminated and Unsubstituted Alkanethiols on Gold " Electroactive Self–Assembled Monolayers,*J. Am. Chem. Soc.*, 112:4301–4306 (1990).

Chrisey, et al., "Covalent attachment of synthetic DNA to self–assembled monolayer films," *Nucleic Acids Research*, 24(15):3031–3039 (1996).

(List continued on next page.)

*Primary Examiner*—Ponnathapu Achutamurthy
*Attorney, Agent, or Firm*—Flehr, Hohbach Test Albritton & Herbert; Richard F. Trecartin, Esq.; Robin M. Silva, Esq.

[57] ABSTRACT

The invention relates to novel methods and compositions for the detection of analytes using the nuclear reorganization energy, $\lambda$, of an electron transfer process.

64 Claims, No Drawings

OTHER PUBLICATIONS

Clery, "DNA Goes Electric," *Science*, 267:1270 (1995).

*Commerce Business Daily* Issue of Sep. 26, 1996 PSA#1688.

Database WPI, Derwent Publications Ltd., London, GB; AN 88–320199 & JP, A, 53 238 166 (Mitsubishi Denki KK), Oct. 4, 1988.

Davis. L. M., et al., "Electron Donor Properties of the Antitumor Drug Amsacrine as Studied by Fluorescence Quenching of DNA–Bound Ethidium," *Chem.–Biol. Interactions*, 62:45–58 (1987).

Davis, J., et al., "Elements of biosensor construction," *Enzyme Microb. Technol.* 17:1030–1035 (1995).

Degani et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.* 110:2615–2620 (1988).

Degani, Y., et al., "Electrical Communication between Redox Centers of Glucose Oxidase and Electrodes via Electrostatically and Covalently Bound Redox Polymers," *J. Am. Chem. Soc.*, 111:2357–2358 (1989).

Degani, Y., et al., "Direct Electrical Communication between Chemically Modified Enzymes and Metal Electrodes. 1. Electron Transfer from Glucose Oxidase to Metal Electrodes via Electron Relays, Bound Covalently to the Enzyme," *J. Phys. Chem.*, 91(6):1285–1288 (1987).

Deinhammer, R.S., et al., "Electronchemical Oxidation of Amine–containing compounds: A Route to the Surface Modification of glassy carbon electrodes," *Langmuir*, 10:1306–1313 (1994).

Dreyer, G. B., et al., "Sequence–specific cleavage of single–stranded DNA: Oligodeocynucleotide–EDTA•Fe(II)," *Proc. Natl. Acad. Sci. USA*, 82:968–972 (1985).

Durham, B., et al., "Photoinduced Electron–Transfer Kinetics of Singly Labeled Ruthenium Bis(bipyridin) Dicarboxybipyridine Cytochrome c Derivatives," *Biochemistry*, 28:8659–8665 (1989).

Durham, B., et al., "Electron–Transfer Kinetics of Singly Labeled Ruthenium(II) Polypyridine Cytochrome c Derivatives," *Advances in Chemistry Series*, 226:181–193 (1990).

Elias, H., et al., "Electron–Transfer Kinetics of Zn–Substituted Cytochrome c and Its $Ru(NH_3)_5$(Histidine–33) Derivative," *J. Am. Chem. Soc.*, 110:429–434 (1988).

Farver, O., et al., "Long–range intramolecular electron transfer in azurins," *Proc. Natl. Acad. Sci. USA*, 86:6968–6972 (1989).

Fox, L. S., et al., "Gaussian Free–Energy Dependence of Electron–Transfer Rates in Iridium Complexes," *Science*, 247:1069–1071 (1990).

Fox, M. A., et al., "Light–Harvesting Polymer Systems," *C&EN*, pp. 38–48 (Mar. 15, 1993).

Francois, J–C., et al., "Periodic Cleavage of Poly(dA) by Oligothymidylates Covalently Linked to the 1,10–Phenanthroline–Copper Complex," *Biochemistry*, 27:2272–22767 (1988).

Friedman, A. E., et al., "Molecular 'Light Switch' for DNA: $Ru(bpy)_2(dppz)^{2+}$," *J. Am. Chem. Soc.*, 112:4960–4962 (1990).

Fromherz, P., et al., "Photoinduced Electron Transfer in DNA Matrix from Intercalated Ethidium to Condensed Methylviologen," *J. Am. Chem. Soc.*, 108:5361–5362 (1986).

Gardner, et al., "Application of conducting polymer technology in microsystem," *Sensors and Actuators*, A51:57–66 (1995).

Gregg, B. A., et al., "Cross–linked redox gels containing glucose oxidase for amperometric biosensor applications," *Anal. Chem.*, 62:258–263 (1990).

Gregg, B. A., et al., "Redox Polymer Films Containing Enzymes. 1. A Redox–Conducting Epoxy Cement: Synthesis, Characterization, and Electrocatalytic Oxidation of Hydroquinone," *J. Phys. Chem.*, 95:5970–5975 (1991).

Hashimoto, et al., "Sequence–Specific Gene Detection with a Gold Electrode Modified with DNA Probes and an Electrochemically Active Dye," *Anal. Chem.* 66:3830–3833 (1994).

Hegner, et al., "Immobilizing DNA on gold via thiol modification for atomic force microscopy imaging in buffer solutions," *FEBS* 336(3):452–456 (1993).

Heller, A., et al., "Amperometric biosensors based on three–dimensional hydrogel–forming epoxy networks," *Sensors and Actuators*, 13–14:180–183 (1993).

Heller, A., "Electrical Wiring of Redox Enzymes," *Acc. Chem. Res.*, 23:128–134 (1990).

Heller et al., "Fluorescent Energy Transfer Oligonucleotide Probes," *Fed. Proc.* 46(6):1968 (1987) Abstract No. 248.

Ho "DNA–Mediated Electron Transfer and Application to 'Biochip' Development," *Abstract. Office of Naval Research* (Report Date: Jul. 25, 1991) 1–4, RR04106.

Hobbs et al., "Polynucleotides Containing 2'–Amino–2'deoxyribose and 2'–Azido–2'–deoxyriose," *Biochemistry*, 12(25):5138–5145 (1973).

Hsung, et al., "Synthesis and Characterization of Unsymmetric Ferrocene–Terminated Phenylethynyl Oligomers," *Organometallics*, 14:4808–4815 (1995).

Hsung, et al., "Thiophenol Protecting Groups for the Palladium–Catalyzed Heck Reaction: Efficient Syntheses of Conjugated Arylthiols," *Tetrahedron Letters*. 36(26):4525–4528 (1995).

Jenkins et al., A Sequence–Specific Molecular Light Switch: Tebhering of an Oligonucleotide to a Dipyridophenazine Complex of Ruthenium (II), *J. Am. Chem. Soc.*, 114:8736–8738 (1992).

Katritzky, et al., "Pyridylethylation—A New Protection Method for Active Hydrogen Compounds," *Tetrahedron Letters*, 25(12):1223–1226 (1984).

Kelley, S.O. and J.K. Barton, "Electrochemistry of Methylene Blue Bound to a DNA–Modified Electrode," *Bioconjugate Chem.*, 8:31–37 (1997).

Kojima et al., "A DNA Probe of Ruthenium Bipyridine Complex Using Photocatalytic Activity," *Chemistry Letter*, pp. 1889–1982 (1989).

Laviron, E., "A.C. Polarography and Fradaic Impedance of Strongly Adsorbed Electroactive Species. Part I: Theoretical and Experimental Study of a Quasi–Reversible Reaction in the Case of a Langmuir Isotherm," *J. Electroanal. Chem.*, 97:135–149 (1979).

Laviron, E., "A.C. Polarography and Faradaic Impedance of Strongly Adsorbed Electroactive Species. Part III: Theoretical Complex Plane Analysis for a Surface Redox Reaction," *J. Electroanal. Chem.*, 105:35–42 (1979).

Lee, et al., "Direct Measurement of the Forces Between Complementary Strands of DNA," *Science*, 266:771–773 (1994).

Lenhard, J.R., et al., "Part VII Covalent Bonding of a Reversible–Electrode Reactanbt to Pt Electrodes Using an organosilane Reagent" *J. Electronal. Chem.*, 78:195–201 (1977).

Lipkin "Identifying DNA by the Speed of Electrons," *Science News*, 147(8):117 (1995).

Maskos, et al., "Oligonucleotide hybridisations on glass supports: a novel linker for oligonucleotide synthesis and hybridisation properties of oligonucleotides synthesised in situ," *Nucleic Acids Research*, 20(7):1679–1684 (1992).

McGee, et al., "2'–Amino–2'–deoxyuridine via an Intramolecular Cyclization of a Tricloroacetimidate," *J. Org. Chem.*, 61:781–785 (1996).

Meade, T. J., "Driving–Force Effects on the Rate of Long–Range Electron Transfer in Ruthenium–Modified Cytochrome c," *J. Am. Chem. Soc.*, 111:4353–4356 (1989).

Meade, T. J., et al., "Electron Transfer through DNA: Site–Specific Modification of Duplex DNA with Ruthenium Donors and Acceptors," *Angew Chem. Int. Ed. Engl.*, 34:352 (1995).

Mestel, "'Electron Highway' Points to Identify of DNA," *New Scientist*, p. 21 (1995).

Millan, et al., "Voltammetric DNA Biosensor for Cystic Fibrosis Based on a Modified Carbon Paste Electrode," *Anal. Chem.*, 66:2943–2948 (1994).

Millan, K.M., et al., "Covalent Immobilization of DNA onto Glassy Carbon Electrodes," *Electroanalysis*, 4(10);929–932 (1992).

Millan, K.M. and Mikkelsen, S.R., "Sequence–Selective Biosensor for DNA Based on Electroactive Hybridization Indicators," *Anal. Chem.*, 65:2317–2323 (1993).

Miller, C., "Absorbed ω–Hydroxy Thiol Monolayers on Gold Electrodes: Evidence for Electron Tunneling to Redox Species in Solution," *J. Phys. Chem.*, 95:877–886 (1991).

Murphy, C. J., et al., "Long–Range Photoinduced Electron Transfer Through a DNA Helix," *Science*, 262:1025–1029 (1993).

Orellana, G., et al., "Photoinduced Electron Transfer Quenching of Excited Ru(II) Polypyridyls Bound to DNA: The Role of the Nucleic Acid Double Helix," *Photochemistry and Photobiology*, 54(4):499–509 (1991).

Palecek, "From Polarography of DNA to Microanalysis with Nucleic Acid–Modified Electrodes, " *Electroanalysis.* 8(1):7–14 (1996).

Purugganan, M. D., et al., Accelerated Electron Transfer Between Metal Complexes Mediated by DNA, *Science*, 241:1645–1649 (1988).

Rhodes, D. And A. Klug, "Helical Periodicity of DNA Determined by Enzyme Digestion," *Nature*, 286:573–578 (1980).

Risser, S. M., et al., "Electron Transfer in DNA: Predictions of Exponential Growth and Decay of Coupling with Donor–Acceptor Distance," *J. Am. Chem. Soc.*, 115(6):2508–2510 (1993).

Sato, Y., et al., "Unidirectional Electron Transfer at Self–Assembled Monolayers of 11–Ferrocenyl–1–undecanethiol on Gold," *Bull. Chem. Soc. Jpn.*, 66(4):1032–1037 (1993).

Satyanarayana, S., et al., "Neither Δ– nor –Tris(phenanthroline)ruthenium(II) Binds to DNA by Classical Intercalation," *Biochemistry*, 31(39):9319–9324 (1992).

Schreiber, et al., "Bis(purine) Complexes of trans-$a_2Pt^{II}$:Preparation and X–ray Structures of Bis(9–methyladenine) and Mixed 9–Methyladenine, 9–Methylguanine Complexes and Chemistry Relevant to Metal–Modified Nucelobase Triples and Quartets," *J. Am. Chem. Soc.* 118:4124–4132 (1996).

Schuhmann, W., et al., "Electron Transfer between Glucose Oxidase and Electrodes via Redox Mediators Bound with Flexible Chains to the Enzyme Surface," *J. Am. Chem. Soc.*, 113:1394–1397 (1991).

Schumm, et al., "Iterative Divergent/Convergent Approach to Linear Conjugated Oligomers by Successive Doubling of the Molecular Length: A Rapid Route to a 128 Å–Long Potential Molecular Wire," *Angew. Chem. Int. Ed. Engl.*, 33(11):1360–1363 (1994).

Sigal et al., "A Self–Assembled Monolayer for the Binding and Study of Histidine–Tagged Proteins by Surface Plasmon Resonance," *Anal. Chem.*, 68(3):490–497 (1996).

Southern, et al., "Arrays of complementary oligonucleotides for analysing the hybridisation behaviour of nucleic acids," *Nucleic Acids Research*, 22(8):1368–1373 (1994).

Strobel, S. A., et al., "Site–Specific Cleavage of a Yeast Chromosome by Oligonucleotide–Directed Triple–Helix Formation," *Science*, 249:73–75 (1990).

Su, et al., "Interfacial Nucleic Acid Hybridization Studied by Random Primer $^{32}P$ Labelling and Liquid–Phase Acoustic Network Analysis," *Analytical Chemistry*, 66(6):769–777 (1994).

Telser, J., et al., "DNA Duplexes Covalently Labeled at Two Sites: Synthesis and Characterization by Steady–State and Time–Resolved Optical Spectroscopies," *J. Am. Chem. Soc.*, 111:7226–7232 (1989).

Telser, J., et al., "DNA Oligomers and Duplexes Containing a Covalently Attached Derivative of Tris(2,2'–bipyridine)ruthenium(II): Synthesis and Characterization by Thermodynamic and Optical Spectroscopic Measurements," *J. Am. Chem. Soc.*, 111:7221–7226 (1989).

Tour, "Conjugated Macromolecules of Precise Length and Constitution. Organic Synthesis for the Construction of Nanoarchitectures," *Chem. Rev.*, 95:537–553 (1996).

Tour, et al., "Self–Assembled Monolayers and Multilayers of Conjugated Thiols, α–ω–Dithiols, and Thioacetyl–Containing Adsorbates. Understanding Attachments between Potential Molecular Wires and Gold Surfaces," *J. Am. Chem. Soc.*, 117:9529–9534 (1995).

Tullius, T.D. and B.A. Dombroski, "Iron(II) EDTA Used to Measure the Helical Twist Along Any DNA Molecule," *Science*, 230:679–681 (1985).

Turro, N., et al. "Photoelectron Transfer Between Molecules Adsorbed in Restricted Spaces," *Photochem. Convers. Storage Sol. Energy, Proc. Int. Conf., 8th*, pp. 121–139 (1990).

Turro, N. J., et al., "Molecular Recognition and Chemistry in Restricted Reaction Spaces. Photophysics and Photoinduced Electron Transfer on the Surfaces of Micelles, Dendrimers, and DNA," *Acc. Chem. Res.*, 24:332–340 (1991).

Uosake, K., et al., "A Self–Assembled Monolayer of Ferrocenylalkane Thiols on Gold as an Electron Mediator for the Reduction of Fe(III)–EDTA in Solution," *Electrochemica Acta.*, 36(11/12):1799–1801 (1991).

Van Ness, J., et al., "A Versatile Solid Support System for Oligodeoxynucleotide Probe–Based Hybridization Assays," *Nucleic Acids Research*, 19(12):3345–3349 (1991).

Weber, et al., "Voltammetry of Redox–Active Groups Irreversibly Adsorbed onto Electrodes. Treatment Using the Marcus Relation between Rate and Overpotential," *Anal. Chem.*, 66:3164–3172 (1994).

Williams, et al., "Studies of oligonucleotide interactions by hybridisation to arrays: the influence of dangling ends on duplex yield," *Nucleic Acids Research*, 22(8):1365–1367 (1994).

Winkler, J. R., et al., "Electron Transfer in Ruthenium–Modified Proteins," *Chem. Rev.*, 92:369–379 (1992).

Xu, et al., "Immobilization of DNA on an Aluminum(III) alkaneobisphosphonate Thin Film with Electrogenerated Chemiluminescent Detection," *J. Am. Chem. Soc.*, 116:8386–8387 (1994).

Xu, et al., "Immobilization and Hybridization of DNA on an Aluminum(III) Alkanebisphosphonate Thin Film with Electrogenerated Chemiluminescent Detection," *J. Am. Chem. Soc.*, 117:2627–2631 (1995).

Yang, et al., "Growth and Characterization of Metal(II) Alkaneobisphosphonate Multilayer Thin Films on Gold Surfaces," *J. Am. Chem. Soc.*, 115:118755–11862 (1993).

Zhou, et al., "Fluorescent Chemosensors Based on Energy Migration in Conjugated Polymers: The Molecular Wire Approach to Increased Sensitivity," *J. Am. Chem. Soc.*, 117:12593–12602 (1995).

Mucic et al., "Synthesis and Characterization of DNA with Ferrocenyl Groups Attached to their 5'–Termini: Electrochemical Characterization of a Redox–Active Nucleotide Monolayer," *Chem. Commun.*, pp. 555–557 (1996).

Carr et al., "Novel Electrochemical Sensors for Neutral Molecules," *Chem. Commun.*, 1649–1650 (1997).

Carter et al., "Voltammetric Studies of the Interaction of Metal Chelates with DNA. 2. Tris–Chelated Complexes of Cobalt(III) and Iron(II) with 10–Phenanthroline and 2,2'–Bipyridine," *J. Am. Chem. Soc.*, 11:8901–8911 (1989).

Johnston et al., "Trans–Dioxorhenium(V)–Mediated Electrocatalytic Oxidation of DNA at Indium Tin–Oxide Electrodes: Voltammetric Detection of DNA Cleavage in Solution," *Inorg. Chem.*, 33:6388–6390 (1994).

Korri–Youssoufi et al., "Toward Bioelectronics: Specific DNA Recognition Based on an Oligonucleotide–Functionalized Polypyrrole," *J. Am. Chem. Soc.*, 119(31):7388–7389 (1997).

Gray et al., "Electron Transfer in Proteins," *Annu. Rev. Biochem.*, 65:537–561 (1996).

Bignozzi et al., "A Simple Poly(pyridine)ruthenium(II) Photosensitizer: (2,2'–Bipyridine)tetracyanoruthenate(II)," *J. Am. Chem. Soc.*, 108:7872–7873 (1986).

Elliott et al., "Electrochemistry, Spectroelectrochemistry, and Photochemistry of a Series of New Covalently Linked Tris (2,2'–bipyridine)ruthenium(II)/Diquat Complexes," *J. Am. Chem. Soc.*, 107:4647–4655 (1985).

Tsukahara, "Kinetics and Mechanisms of Reduction of Metmyoglobins. Importance of the Geometry Change at the Heme Iron Site upon Reduction," *J. Am. Chem. Soc.*, 111:2040–2044 (1989).

Winkler et al., "Rapid electron injection into multisite metalloproteins: intramolecular electron transfer in cytochrome oxidase," *Biophysical Chemistry*, 54:199–209 (1995).

Gray et al., "Long–Range Electron Transfer in Multisite Metalloproteins," *Biochemistry*, 28(19)7499–7504 (1989).

DETECTION OF ANALYTES USING REORGANIZATION ENERGY

This application is a continuing application of U.S. Ser. No. 08/873,977, filed Jun. 12, 1997.

FIELD OF THE INVENTION

The invention relates to novel methods and compositions for the detection of analytes based on changes in the nuclear reorganization energy, $\lambda$, of electron transfer process.

BACKGROUND OF THE INVENTION

Electron transfer reactions are crucial steps in a variety of biological transformations ranging from photosynthesis to aerobic respiration. Studies of electron transfer reactions in both chemical and biological systems have led to the development of a large body of knowledge and a strong theoretical base, which describes the rate of electron transfer in terms of a definable set of parameters.

Electronic tunneling in proteins and other biological molecules occurs in reactions where the electronic interaction of the redox centers is relatively weak. Semiclassical theory reaction predicts that the reaction rate for electron transfer depends on the driving force ($-\Delta G°$), a nuclear reorganization parameter ($\lambda$), and the electronic-coupling strength ($H_{AB}$) between the reactants and products at the transition state, according to the following equation:

$$k_{ET} = (4\pi^3/h^2 \lambda k_B T)^{1/2} (H_{AB})^2 exp[(-\Delta G° + \lambda)^2 / \lambda k_B T]$$

The nuclear reorginzation energy, $\lambda$, in the equation above is defined as the energy of the reactants at the equilibrium nuclear configuration of the products. There are two components of $\lambda$; "outer sphere" effects ($\lambda_o$) and "inner sphere" effects ($\lambda_i$). For electron transfer reactions in polar solvents, the dominant contribution to $\lambda$ arises from the reorientation of solvent molecules in response to the change in charge distribution of the reactants. The second component of $\lambda$ comes from the changes in bond lengths and angles due to changes in the oxidation state of the donors and acceptors.

It is an object of the present invention to provide methods for the detection of target analytes exploiting changes in the solvent reorganization energy of electron transfer reactions.

SUMMARY OF THE INVENTION

In accordance with the above objects, the present invention provides methods of detecting a target analyte in a test sample. The method comprises binding an analyte to a redox active complex. The redox active complex comprises a solvent accessible transition metal complex having at least one coordination site occupied by a polar coordination group and a binding ligand which will bind the target analyte. The complex is bound to an electrode. Upon binding, a solvent inhibited transition metal complex is formed and electron transfer is detected between the solvent inhibited transition metal complex and the electrode. The methods also include applying at least a first input signal to the solvent inhibited transition metal complex.

In a further aspect, the invention provides methods of detecting a target analyte in a test sample comprising associating an analyte with a redox active complex. The redox active complex comprises a solvent inhibited transition metal complex, and a binding ligand which will bind the target analyte. Upon association, a solvent accessible transition metal complex is formed, which is then detected.

In an additional aspect, the invention provides methods of detecting a target analyte in a test sample comprising associating an analyte with a redox active complex. The complex comprises a solvent inhibited transition metal complex, a binding ligand which will bind the target analyte, and an analyte analog. The complex is bound to an electrode, and upon association, a solvent accessible transition metal complex is formed, which is then detected.

In a further aspect, the invention provides compositions comprising an electrode with a covalently attached redox active complex. The complex comprises a binding ligand and a solvent accessible redox active molecule, which has at least one, and preferably two or three coordination sites occupied by a polar coordination group, one or more of which may be a water molecule.

In a further aspect, the present invention provides an apparatus for the detection of target analytes in a test sample, comprising a test chamber comprising a first and a second measuring electrode. The first measuring electrode comprises a covalently attached redox active complex comprising a solvent accessible transition metal complex, preferably having at least three coordination sites occupied by a polar coordination group, and a binding ligand. The apparatus further comprises an AC/DC voltage source electrically connected to the test chamber, and an optional signal processor for detection.

DETAILED DESCRIPTION

The present invention provides methods and compositions for the detection of target analytes using changes in the solvent reorganization energy of transition metal complexes upon binding of the analytes, to facilitate electron transfer between the transition metal complex and an electrode. This invention is based on the fact that a change in the oxidation state of a redox active molecule such as a transition metal ion, i.e. upon the acceptance or donation of an electron, results in a change in the charge and size of the metal ion. This change in the charge and size requires that the surrounding solvent reorganize, to varying degrees, upon this change in the oxidation state.

For the purposes of this invention, the solvent reorganization energy will be treated as the dominating component of $\lambda$. Thus, if the solvent reorganization energy is high, a change in the oxidation state will be impeded, even under otherwise favorable conditions.

In conventional methodologies using electron transfer, this solvent effect is minimized by using transition metal complexes that minimize solvent reorganization at the redox center, generally by using several large hydrophobic ligands which serve to exclude water. Thus, the ligand for the transition metal ions traditionally used are non-polar and are generally hydrophobic, frequently containing organic rings.

However, the present invention relies on the novel idea of exploiting this solvent reorganization energy to serve as the basis of an assay for target analytes. In the present invention, transition metal complexes that are solvent accessible, i.e. have at least one, and preferably more, small, polar ligands, and thus high solvent reorganization energies, are used. Thus, at initiation energies less than the solvent reorganization energy, no significant electron transfer occurs. However, upon binding of a generally large target analyte, the transition metal complexes becomes solvent inhibited, inaccessible to polar solvents generally through steric effects, which allows electron transfer at previously inoperative initiation energies.

Thus, the change in a transition metal complex from solvent accessible to solvent inhibited serves as a switch or trigger for electron transfer. This thus becomes the basis of an assay for an analyte. Closs and Miller have shown that there is a decrease in lambda in nonpolar solvents in their work on Donor(bridge)Acceptor electron transfer reactions in solution. (Closs and Miller, Science, 240, 440–447, (1988). This idea also finds conceptual basis in work done with metmyoglobin, which contains a coordinated water molecule in the hexacoordinate heme iron site and does not undergo self-exchange very rapidly (rate constant $k_{22}$ $1M^{-1}s^{-1}$). Upon chemical modification, the heme becomes pentacoordinate, removing the water, and the self-exchange rate constant increases significantly (rate constant $k_{22}$ $1 \times 10^4$ $M^{-1}s^{-1}$); see Tsukahara, J. Am. Chem. Soc. 111:2040 (1989).

Without being bound by theory, there are two general mechanisms which may be exploited in the present invention. In a preferred embodiment, the binding of a target analyte to a binding ligand which is sterically close to a solvent accessible transition metal complex causes one or more of the small, polar ligands on the solvent accessible transition metal complex to be replaced by one or more coordination atoms supplied by the target analyte, causing a decrease in the solvent reorganization energy for at least two reasons. First, the exchange of a small, polar ligand for a generally larger, nonpolar ligand that will generally exclude more water from the metal, lowering the required solvent reorganization energy (i.e. an inner sphere $\lambda_i$ effect). Secondly, the proximity of a generally large target analyte to the relatively small redox active molecule will sterically exclude water within the first or second coordination sphere of the metal ion, also decreasing the solvent reorganization energy.

Alternatively, a preferred embodiment does not necessarily require the exchange of the polar ligands on the metal ion by a target analyte coordination atom. Rather, in this embodiment, the polar ligands are effectively irreversibly bound to the metal ion, and the decrease in solvent reorganization energy is obtained as a result of the exclusion of water in the first or second coordination sphere of the metal ion as a result of the binding of the target analyte; essentially the water is excluded (i.e. an outher sphere $\lambda_o$ effect).

Accordingly, the present invention provides methods for the detection of target analytes. The methods generally comprise binding an analyte to a binding ligand that is either associated with (forming a redox active complex) or near to a transition metal complex. The transition metal complex is bound to an electrode generally through the use of a conductive oligomer. Upon analyte binding, the reorganization energy of the transition metal complex decreases to form a solvent inhibited transition metal complex, to allow greater electron transfer between the solvent inhibited transition metal complex and the electrode.

Accordingly, the present invention provides methods for the detection of target analytes. By "target analyte" or "analyte" or grammatical equivalents herein is meant any molecule, compound or particle to be detected. As outlined below, target analytes preferably bind to binding ligands, as is more fully described below.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eucaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

By "nucleic acid" or "oligonucleotide" or grammatical equivalents herein means at least two nucleotides covalently linked together. A nucleic acid of the present invention will generally contain phosphodiester bonds, although in some cases, as outlined below, a nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Nucleic acids containing one or more carbocyclic sugars are also included within the definition of nucleic acids (see Jenkins et al., Chem. Soc. Rev. (1995) pp169–176). These modifications of the ribose-phosphate backbone may be done to facilitate the addition of moieties, or to increase the stability and half-life of such molecules in physiological environments.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine and hypoxathanine, etc. As used herein, the term "nucleoside" includes nucleotides, and modified nucleosides such as amino or thio modified nucleosides.

By "proteins" or grammatical equivalents herein is meant proteins, oligopeptides and peptides, and analogs, including proteins containing non-naturally occuring amino acids and amino acid analogs, and peptidomimetic structures.

As will be appreciated by those in the art, a large number of analytes may be detected using the present methods; basically, any target analyte for which a binding ligand, described below, may be made may be detected using the methods of the invention.

In a preferred embodiment, the target analyte is added or introduced to a redox active complex, which is preferably attached to an electrode. By "redox active complex" herein is meant a complex comprising at least one transition metal complex and at least one binding ligand, which, as more fully described below, may be associated in a number of different ways. By "transition metal complex" or "redox active molecule" or "electron transfer moiety" herein is meant a metal-containing compound which is capable of reversibly or semi-reversibly transfering one or more electrons. It is to be understood that electron donor and acceptor capabilities are relative; that is, a molecule which can lose an electron under certain experimental conditions will be able to accept an electron under different experimental conditions. It is to be understood that the number of possible transition metal complexes is very large, and that one skilled in the art of electron transfer compounds will be able to utilize a number of compounds in the present invention. Transition metals are those whose atoms have a partial or complete d shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are metals that do not change the number of coordination sites upon a change in oxidation state, including ruthenium, osmium, iron, platinium and palladium, with ruthenium and iron being especially preferred. Generally, transition metals are depicted herein as M.

The transition metal ions are complexed with ligands that serve to provide the coordination atoms for the binding of the metal ion. Generally, it is the composition or characteristics of the ligands that determine whether a transition metal complex is solvent accessible. By "solvent accessible transition metal complex" or grammatical equivalents herein is meant a transition metal complex that has at least one, preferably two, and more preferably three, four or more small polar ligands. The actual number of polar ligands will depend on the coordination number (n) of the metal ion. Preferred numbers of polar ligands are (n−1) and (n−2). For example, for hexacoordinate metals, such as Fe, Ru, and Os, solvent accessible transition metal complexes preferably have one to five small polar ligands, with two to five being preferred, and three to five being particularly preferred, depending on the requirement for the other sites, as is more fully described below. Tetracoordinate metals such as Pt and Pd preferably have one, two or three small polar ligands.

It should be understood that "solvent accessible" and "solvent inhibited" are relative terms. That is, at high applied energy, even a solvent accessible transition metal complex may be induced to transfer an electron.

The other coordination sites of the metal are used for attachment of the transition metal complex to either a binding ligand (directly or indirectly using a linker), to form a redox active complex, or to the electrode (frequently using a spacer, as is more fully described below), or both. Thus for example, when the transition metal complex is directly joined to a binding ligand, one, two or more of the coordination sites of the metal ion may be occupied by coordination atoms supplied by the binding ligand (or by the linker, if indirectly joined). In addition, or alternatively, one or more of the coordination sites of the metal ion may be occupied by a spacer used to attach the transition metal complex to the electrode. For example, when the transition metal complex is attached to the electrode separately from the binding ligand as is more fully described below, all of the coordination sites of the metal (n) except 1 (n−1) may contain polar ligands.

Suitable small polar ligands, generally depicted herein as "L", fall into two general categories, as is more fully described below. In one embodiment, the small polar ligands will be effectively irreversibly bound to the metal ion, due to their characteristics as generally poor leaving groups or as good sigma donors, and the identity of the metal. These ligands may be referred to as "substitutionally inert". Alternatively, as is more fully described below, the small polar ligands may be reversibly bound to the metal ion, such that upon binding of a target analyte, the analyte may provide one or more coordination atoms for the metal, effectively replacing the small polar ligands, due to their good leaving group properties or poor sigma donor properties. These ligands may be referred to as "substitutionally labile". The ligands preferably form dipoles, since this will contribute to a high solvent reorganization energy.

Irreversible ligand groups include, but are not limited to, amines (—$NH_2$, —NHR, and —$NR_2$, with R being a substitution group that is preferably small and hydrophilic, as will be appreciated by those in the art), cyano groups (—C≡N), thiocyano groups (—SC≡N), and isothiocyano groups (—N≡CS). Reversible ligand groups include, but are not limited to, $H_2O$ and halide atoms or groups. It should be understood that the change in solvent reorganization energy is quite high when a water molecule serves as a coordination atom; thus, the replacement or addition of a single water molecule on a redox active molecule will generally result in a detectable change, even when the other ligands are not small polar ligands. Thus, in a preferred embodiment, the invention relies on the replacement or addition of at least one water molecule on a redox active molecule.

In addition to small polar ligands, the metal ions may have additional, hydrophobic ligands, also depicted herein as "L". That is, a hexacoordinate metal ion such as Fe may have one ligand position (preferably axial) filled by the spacer used for attachment to the electrode, two ligand positions filled by phenanthroline, and two or three small polar ligands, depending on the linkage to the binding ligand. As will be appreciated by those in the art, a wide variety of suitable ligands may be used. Suitable traditional ligands include, but are not limited to, isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam), isocyanide and metallocene ligands. Substituted derivatives, including fused derivatives, may also be used.

The presence of at least one small, polar ligand on the transition metal complex makes the solvent reorganization energy high, which suppresses electron transfer to and from the transition metal redox active molecule. Thus, in a preferred embodiment, a solvent accessible redox active molecule has a solvent reorganization energy of greater than about 500 meV, with greater than about 800 meV being preferred, greater than about 1 eV being especially preferred and greater than about 1.2 to 1.3 eV being particularly preferred.

In addition to the solvent accessible redox active molecule, a redox active complex comprises a binding ligand which will bind the target analyte. By "binding ligand" or grammatical equivalents herein is meant a compound that is used to probe for the presence of the target analyte, and that will specifically bind to the analyte; the binding ligand is part of a binding pair. By "specifically bind" herein is meant that the ligand binds the analyte, with specificity sufficient to differentiate between the analyte and other components or contaminants of the test sample. This binding should be sufficient to remain bound under the conditions of the assay, including wash steps to remove non-specific binding. Generally, the disassociation constants of the analyte to the binding ligand will be in the range of at least $10^{-4}$–$10^{-6}$ $M^{-1}$, with a preferred range being $10^{-5}$ to $10^{-9}$ $M^{-1}$ and a particularly preferred range being $10^{-7}$–$10^{-9}$ $M^{-1}$.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand may be a complementary nucleic acid. Alternatively, the binding ligand may be a nucleic acid-binding protein when the analyte is a single or double-stranded nucleic acid. When the analyte is a protein, the binding ligands include proteins or small molecules. Preferred binding ligand proteins include peptides. For example, when the analyte is an enzyme, suitable binding ligands include substrates and inhibitors. Antigen-antibody pairs, receptor-ligands, and carbohydrates and their binding partners are also suitable analyte-binding ligand pairs.

In general, preferred embodiments utilize relatively small binding ligands and larger target analytes.

Together, the transition metal complex and the binding ligand comprise a redox active complex. In addition, there may be more than one binding ligand or transition metal complex per redox active complex. The redox active complex may also contain additional moieties, such as cross-linking agents, labels, etc., and linkers for attachment to the electrode.

The redox active complex is bound to an electrode. This may be accomplished in any number of ways, as will be apparent to those in the art. Generally, as is more fully described below, one or both of the transition metal complex and the binding ligand are attached, via a spacer, to the electrode.

In a preferred embodiment, the redox active complex is covalently attached to the electrode via a spacer. By "spacer" herein is meant a moiety which holds the redox active complex off the surface of the electrode. In a preferred embodiment, the spacer is a conductive oligomer as described herein, although suitable spacer moieties include passivation agents and insulators as outlined below. The spacer moieties may be substantially non-conductive, although preferably (but not required) is that the electron coupling between the redox active molecule and the electrode ($H_{AB}$) does not become the rate limiting step in electron transfer.

In general, the length of the spacer is as described for conductive polymers and passivation agents. As will be appreciated by those in the art, if the spacer becomes too long, the electronic coupling between the redox active molecule and the electrode will decrease.

In a preferred embodiment, the spacer is a conductive oligomer. By "conductive oligomer" herein is meant a substantially conducting oligomer, preferably linear, some embodiments of which are referred to in the literature as "molecular wires". Conductive oligomers, and their synthesis, use and attachment to moieties is described in PCT US97/20014, hereby expressly incorporated in its entirety.

By "substantially conducting" herein is meant that the electron coupling between the transition metal complex and the electrode ($H_{AB}$) throught the oligomer is not the rate limiting step of electron transfer. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to pass electrons into or from an attached transition metal complex. Furthermore, the conductive oligomer is more conductive than the insulators as defined herein.

In a preferred embodiment, the conductive oligomers have a conductivity, S, of from between about $10^{-6}$ to about $10^{-4}$ $\Omega^{-1}cm^{-1}$, with from about $10^{-5}$ to about $10^{3}$ $\Omega^{-1}cm^{-1}$ being preferred, with these S values being calculated for molecules ranging from about 20Å to about 200 Å. As described below, insulators have a conductivity S of about $10^{-7}$ $\Omega^{-1}cm^{-1}$ or lower, with less than about $10^{-8}$ $\Omega^{-1}cm^{-1}$ being preferred. See generally Gardner et al., Sensors and Actuators A 51 (1995) 57–66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during synthesis of the redox active complexes, ii) during the attachment of the conductive oligomer to an electrode, or iii) during analyte assays.

The oligomers of the invention comprise at least two monomeric subunits, as described herein. As is described more fully below, oligomers include homo- and hetero-oligomers, and include polymers.

In a preferred embodiment, the conductive oligomer has the structure depicted in Structure 1:

Structure 1

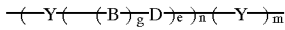

As will be understood by those in the art, all of the structures depicted herein may have additional atoms or structures; i.e. the conductive oligomer of Structure 1 may be attached to transition metal complexes or redox active complexes, binding ligands, electrodes, etc. or to several of these. Unless otherwise noted, the conductive oligomers depicted herein will be attached at the left side to an electrode; that is, as depicted in Structure 1, the left "Y" is connected to the electrode as described herein and the right "Y", if present, is attached to the redox active complex, i.e. either the transition metal complex or binding ligand, either directly or through the use of a linker, as is described herein.

In this embodiment, Y is an aromatic group, n is an integer from 1 to 50, g is either 1 or zero, e is an integer from zero to 10, and m is zero or 1. When g is 1, B—D is a bond able to conjugate with neighboring bonds (herein referred to as a "conjugated bond"), preferably selected from acetylene, alkene, substituted alkene, amide, azo, —C═N— (including —N═C—, —CR═N— and —N═CR—), —Si═Si—, and —Si═C— (including —C═Si—, —Si═CR— and —CR═Si—). When g is zero, e is preferably 1, D is preferably carbonyl, or a heteroatom moiety, wherein the heteroatom is selected from oxygen, sulfur, nitrogen or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise an oligomer of a single type of Y groups, or of multiple types of Y groups. Thus, in a preferred embodiment, when a barrier monolayer is used as is described below, one or more types of Y groups are used in the conductive oligomer within the monolayer with a second type(s) of Y group used above the monolayer level. Thus, as is described herein, the conductive oligomer may comprise Y groups that have good packing efficiency within the monolayer at the electrode surface, and a second type(s) of Y groups with greater flexibility and hydrophilicity above the monolayer level to facilitate target analyte binding. For example, unsubstituted benzyl rings may comprise the Y rings for monolayer packing, and substituted benzyl rings may be used above the monolayer. Alternatively, heterocyclic rings, either substituted or unsubstituted, may be used above the monolayer. Additionally, in one embodiment, heterooligomers are used even when the conductive oligomer does not extend out of the monolayer.

The aromatic group may be substituted with a substitution group, generally depicted herein as R. R groups may be added as necessary to affect the packing of the conductive oligomers, i.e. when the conductive oligomers form a monolayer on the electrode, R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

Suitable R groups include, but are not limited to, hydrogen, alkyl, alcohol, aromatic, amino, amido, nitro, ethers, esters, aldehydes, ketones, iminos, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur, silicon or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —NH$_2$, —NHR and —NR$_2$ groups, with R being as defined herein.

By "nitro group" herein is meant an —NO$_2$ group.

By "sulfur containing moieties" herein is meant compounds containing sulfur atoms, including but not limited to, thia-, thio- and sulfo-compounds, thiols (—SH and —SR), sulfides (—RSR—), sulfoxides (—R—SO—R—), sulfones (—R—SO$_2$—R—), disulfides (—R—S—S—R—) and sulfonyl ester (R—SO$_2$—O—R) groups. By "phosphorus containing moieties" herein is meant compounds containing phosphorus, including, but not limited to, phosphines and phosphates. By "silicon containing moieties" herein is meant compounds containing silicon, including siloxanes.

By "ether" herein is meant an —O—R group.

By "ester" herein is meant a —COOR group; esters include thioesters (—CSOR).

By "halogen" herein is meant bromine, iodine, chlorine, or fluorine. Preferred substituted alkyls are partially or fully halogenated alkyls such as CF$_3$, etc.

By "aldehyde" herein is meant —RCOH groups.

By "ketone" herein is meant —R—CO—R groups.

By "alcohol" herein is meant —OH groups, and alkyl alcohols —ROH.

By "amido" herein is meant —RCONH— or RCONR— groups.

By "imino" herein is meant and —R—CNH—R— and —R—CNR—R—groups.

By "ethylene glycol" herein is meant a —(O—CH$_2$—CH$_2$)$_n$— group, although each carbon atom of the ethylene group may also be singly or doubly substituted, i.e. —(O—CR$_2$—CR$_2$)$_n$—, with R as described above. Ethylene glycol derivatives with other heteroatoms in place of oxygen (i.e. —(N—CH$_2$—CH$_2$)$_n$— or —(S—CH$_2$—CH$_2$)$_n$—, or with substitution groups) are also preferred.

Preferred substitution groups include, but are not limited to, methyl, ethyl, propyl, and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B—D is a bond linking two atoms or chemical moieties. In a preferred embodiment, B—D is a conjugated bond, containing overlapping or conjugated π-orbitals.

Preferred B—D bonds are selected from acetylene (—C≡C—, also called alkyne or ethyne), alkene (—CH=CH—, also called ethylene), substituted alkene (—CR=CR—, —CH=CR— and —CR=CH—), amide (—NH—CO— and —NR—CO— or —CO—NH— and —CO—NR—), azo (—N=N—), esters and thioesters (—CO—O—, —O—CO—, —CS—O— and —O—CS—)

and other conjugated bonds such as (—CH═N—, —CR═N—, —N═CH— and —N═CR—), (—SiH═SiH—, —SiR═SiH—, —SiR═SiH—, and —SiR═SiR—), (—SiH═CH—, —SiR═CH—, —SiH═CR—, —SiR═CR—, —CH═SiH—, —CR═SiH—, —CH═SiR—, and —CR═SiR—). Particularly preferred B—D bonds are acetylene, alkene, amide, and substituted derivatives of these three, and azo. Especially preferred B—D bonds are acetylene, alkene and amide. The oligomer components attached to double bonds may be in the trans or cis conformation, or mixtures. Thus, either B or D may include carbon, nitrogen or silicon. The substitution groups are as defined as above for R. When g=0 in the Structure 1 conductive oligomer, e is preferably 1 and the D moiety may be carbonyl or a heteroatom moiety as defined above.

As above for the Y rings, within any single conductive oligomer, the B—D bonds (or D moieties, when g=0) may be all the same, or at least one may be different. For example, when m is zero, the terminal B—D bond may be an amide bond, and the rest of the B—D bonds may be acetylene bonds. Generally, when amide bonds are present, as few amide bonds as possible are preferable, but in some embodiments all the B—D bonds are amide bonds. Thus, as outlined above for the Y rings, one type of B—D bond may be present in the conductive oligomer within a monolayer as described below, and another type above the monolayer level, to give greater flexibility for nucleic acid hybridization.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient binding of target analytes, the binding should occur at a distance from the surface. For example, it appears that the kinetics of nucleic acid hybridization increase as a function of the distance from the surface, particularly for long oligonucleotides of 200 to 300 basepairs. Accordingly, the length of the conductive oligomer is such that the binding ligand is positioned from about 6 Å to about 100 Å (although distances of up to 500 Å may be used) from the electrode surface, with from about 25 Å to about 60 Å being preferred. Accordingly, n will depend on the size of the aromatic group, but generally will be from about 1 to about 20, with from about 2 to about being preferred and from about 3 to about 10 being especially preferred.

In the structures depicted herein, m is either 0 or 1. That is, when m is 0, the conductive oligomer may terminate in the B—D bond or D moiety, i.e. the D atom is attached to the redox active complex or molecule, or binding ligand, either directly or via a linker. In some embodiments there may be additional atoms, such as a linker, attached between the conductive oligomer and the bound moiety. Alternatively, when m is 1, the conductive oligomer may terminate in Y, an aromatic group, i.e. the aromatic group is attached to the moiety or linker.

As will be appreciated by those in the art, a large number of possible conductive oligomers may be utilized. These include conductive oligomers falling within the Structure 1 and Structure 4 formulas, as well as other conductive oligomers, as are generally known in the art, including for example, compounds comprising fused aromatic rings or Teflon®-like oligomers, such as —(CF$_2$)$_n$—, —(CHF)$_n$— and —(CFR)$_n$—. See for example, Schumm et al., Angew. Chem. Intl. Ed. Engl. 33:1361 (1994); Grosshenny et al., Platinum Metals Rev. 40(1):26–35 (1996); Tour, Chem. Rev. 96:537–553 (1996); Hsung et al., Organometallics 14:4808–4815 (1995; and references cited therein, all of which are expressly incorporated by reference.

Particularly preferred conductive oligomers of this embodiment are depicted below:

Structure 2

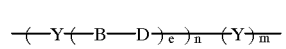

Structure 2 is Structure 1 when g is 1. Preferred embodiments of Structure 2 include: e is zero, Y is pyrole or substituted pyrole; e is zero, Y is thiophene or substituted thiophene; e is zero, Y is furan or substituted furan; e is zero, Y is phenyl or substituted phenyl; e is zero, Y is pyridine or substituted pyridine; e is 1, B—D is acetylene and Y is phenyl or substituted phenyl. A preferred embodiment of Structure 2 is also when e is one, depicted as Structure 3 below:

Structure 3

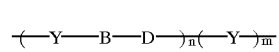

Preferred embodiments of Structure 3 are: Y is phenyl or substituted phenyl and B—D is azo; Y is phenyl or substituted phenyl and B—D is alkene; Y is pyridine or substituted pyridine and B—D is acetylene; Y is thiophene or substituted thiophene and B—D is acetylene; Y is furan or substituted furan and B—D is acetylene; Y is thiophene or furan (or substituted thiophene or furan) and B—D are alternating alkene and acetylene bonds.

In a preferred embodiment, the conductive oligomer has the structure depicted in Structure 4:

Structure 4

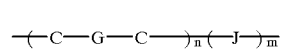

In this embodiment, C are carbon atoms, n is an integer from 1 to 50, m is 0 or 1, J is a heteroatom selected from the group consisting of nitrogen, silicon, phosphorus, sulfur, carbonyl or sulfoxide, and G is a bond selected from alkane, alkene or acetylene, such that together with the two carbon atoms the C—G—C group is an alkene (—CH═CH—), substituted alkene (—CR═CR—) or mixtures thereof (—CH═CR— or —CR═CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma bonds per conductive oligomer being preferred. Alkene bonds are preferred, and are generally depicted herein, although alkane and acetylene bonds may be substituted in any structure or embodiment described herein as will be appreciated by those in the art.

In a preferred embodiment, the m of Structure 4 is zero. In a particularly preferred embodiment, m is zero and G is an alkene bond, as is depicted in Structure 5:

Structure 5

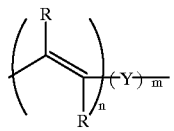

The alkene oligomer of structure 5, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal flexibility of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of Structures 1 and 4.

The conductive oligomers are covalently attached to the redox active complexes, transition metal complexes (collectively redox active moieties), or binding ligands. By "covalently attached" herein is meant that two moieties are attached by at least one bond, including sigma bonds, pi bonds and coordination bonds.

The redox active moiety or binding ligand is covalently attached to the conductive oligomer, and the conductive oligomer is also covalently attached to the electrode. In general, the covalent attachments are done in such a manner as to minimize the amount of unconjugated sigma bonds an electron must travel from the electron donor to the electron acceptor. Thus, linkers are generally short, or contain conjugated bonds with few sigma bonds.

The covalent attachment of the redox active moiety or binding ligand and the conductive oligomer may be accomplished in a variety of ways, and will depend on the composition of the redox active moiety or binding ligand, as will be appreciated by those in the art. Representative conformations of the attachment of redox active complexes to electrodes are depicted below in Structures 6 and 7:

Structure 6

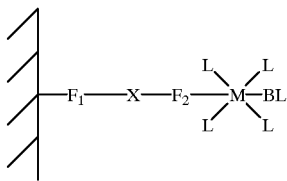

In Structure 6, the hatched marks on the left represent an electrode. X is a conductive oligomer as defined herein. $F_1$ is a linkage that allows the covalent attachment of the electrode and the conductive oligomer, including bonds, atoms or linkers such as are described herein. $F_2$ is a linkage that allows the covalent attachment of the conductive oligomer to the redox active complex, which includes the binding ligand, BL. $F_1$ and $F_2$ may be a bond, an atom or a linkage as is herein described. $F_2$ may be part of the conductive oligomer, part of the redox active complex, or exogenous to both. As for Structure 7, M is the metal ion and L is a co-ligand, as defined herein; as noted above, if a traditional hydrophobic ligand is used, two or more of the depicted L ligands may be part of multidentate ligand, rather than separate ligands. It should be noted that while the BL is depicted in an axial position, this is not required.

In this embodiment, a coordination atom may be contributed directly from the binding ligand; alternatively, there may be a linker that provides a coordination atom and is linked to the binding ligand. A wide variety of linkers can be used herein, as will be appreciated by those in the art. Suitable linkers are known in the art, for example, homo-or hetero-bifunctional linkers as are well known (see 1994 Pierce Chemical Company catalog, technical section on cross-linkers, pages 155–200, incorporated herein by reference). Preferred linkers include, but are not limited to, alkyl groups and alkyl groups containing heteroatom moieties, with short alkyl groups, esters, epoxy groups and ethylene glycol and derivatives being preferred, with propyl, acetylene, and $C_2$ alkene being especially preferred.

Structure 7

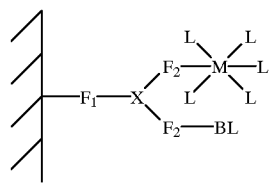

Structure 7 depicts a "branched" conformation, wherein the transition metal complex and the binding ligand are not directly attached. As will be appreciated by those in the art, the transition metal complex and the binding ligand may be attached at the same position on the conductive oligomer, or different positions, and more than one transition metal complex and/or binding ligand may be present.

Structures 6 and 7 depict hexacoordinate metal ions, although as will be appreciated by those in the art, other types of metal ions also find use in the invention, with the appropriate adjustment of L ligands.

The attachment of the metal ion is generally done by attaching a substitutionally inert ligand to the end of the spacer. In a preferred embodiment, this ligand is monodentate, or at most bidentate, although other polydentate ligands may also be used. Thus, for example, an amino or imidazole group (monodentate) or a phenathroline (bidentate) may be attached to the end of the spacer using techniques well known in the art, or techniques outlined in PCT US97/20014, hereby expressly incorporated by reference.

The attachment of the binding ligand to either the metal ion or the spacer is also done using well known techniques, and will depend on the composition of the binding ligand. When the binding ligand is a nucleic acid, either double-stranded or single-stranded, attachment to the metal ion can be done as is described in PCT US97/20014.

In general, attachment of the binding ligand to either the metal ion or the spacer is done using functional groups either naturally found on the binding ligand or added using well known techniques. These groups can be at the terminus of the binding ligand, for example at the N- or C-terminus of a protein, or at any internal position. Thus, amino, thio, carboxyl or amido groups can all be used for attachment. Similarly, chemical attachment of traditional ligands such as pyridine or phenanthroline may also be done, as will be appreciated by those in the art. For example, attachment of proteinaceous binding ligands is generally done using functional groups present on the amino acid side chains or at the N- or C-terminus; for example, any groups such as the N-terminus or side chains such as histidine may serve as ligands for the metal ion. Similarly, attachment of carbohydrate binding ligands is generally done by derivatizing the sugar to serve as a metal ion ligand. Alternatively, these groups may be used to attach to the spacer, using well known techniques. In any of these embodiments, there may be additional connector or linkers present. For example, when the binding ligand is a proteinaceous enzyme substrate or inhibitor, there may be additional amino acids, or an alkyl group, etc., between the metal ion ligand and the functional substrate or inhibitor.

In addition, as noted herein, two or more binding ligands may be attached to a single redox active complex. For example, two single-stranded nucleic acids may be attached, such that the binding of a complementary target sequence will change the solvent reorganization energy of the redox active molecule. In this embodiment, the two single stranded nucleic acids are designed to allow for a "gap" in the complementary sequence to accomodate the metal ion; this is generally from 1 to 3 nucleotides.

In a preferred embodiment, the binding ligand and the redox active molecule do not form a redox active complex, but rather are each individually attached to the electrode, generally via a spacer. In this embodiment, it is the proximity of the redox active molecule to the target analyte bound to the binding ligand that results in a decrease of the solvent reorganization energy upon binding. Preferably, the solvent accessible redox active molecule is within 12 Å of some portion of the target analyte, with less than about 8 Å being preferred and less than about 5 Å being particularly preferred, and less than about 3.5 Å being especially preferred. It should be noted that the distance between the binding ligand and the redox active molecule may be much larger, depending on the size of the target analyte. Thus, the binding of a large target analyte may reduce the solvent reorganization energy of a solvent accessible redox active molecule many angstroms away from the binding ligand. A representative composition is depicted below in Structure 8:

Structure 8

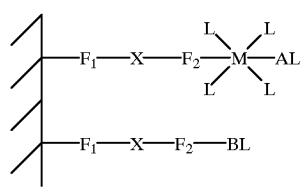

In Structure 8, the binding ligand and the transition metal complex are separately attached to the electrode. While Structure 8 depicts a 1:1 ratio of transition metal complexes to binding ligands, this is not required; in fact, it may be preferable to have an excess of transition metal complexes on the electrode, particularly when the target analyte is relatively large in comparison to the transition metal complex. Thus, for example, a single binding event of a target analyte to a binding ligand can result in a decrease in solvent reorganization energy for a number of transition metal complexes, if the density of the transition metal complexes is high enough in the area of the binding ligand, or the target analyte is large enough. Similarly, different binding ligands for the same target analyte may be used; for example, to "tack down" a large target analyte on the surface, to effect as many transition metal complexes as possible per single target analyte.

The redox moieties and binding ligands are attached to an electrode, via a spacer as outlined above. Thus, one end or terminus of the conductive oligomer is attached to the redox moiety or binding ligand, and the other is attached to an electrode. In some embodiments it may be desirable to have the conductive oligomer attached at a position other than a terminus, or to have a branched conductive oligomer that is attached to an electrode at one terminus and to a redox active molecule and a binding ligand at other termini. Similarly, the conductive oligomer may be attached at two sites to the electrode.

By "electrode" herein is meant a composition, which, when connected to an electronic device, is able to sense a current or charge and convert it to a signal. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays are made, thus requiring addressable locations for both synthesis and detection. Alternatively, for single analyte analysis, the electrode may be in the form of a tube, with the compositions of the invention bound to the inner surface. This allows a maximum of surface area containing the binding ligand to be exposed to a small volume of sample.

The covalent attachment of the conductive oligomer containing the redox active moieties and binding ligands of the invention may be accomplished in a variety of ways, depending on the electrode and the conductive oligomer used. Generally, some type of linker is used. For example, in Structure 6, $F_1$ may be a linker or atom. The choice of "$F_1$" will depend in part on the characteristics of the electrode. Thus, for example, $F_1$ may be a sulfur moiety when a gold electrode is used. Alternatively, when metal oxide electrodes are used, $F_1$ may be a silicon (silane) moiety attached to the oxygen of the oxide (see for example Chen et al., Langmuir 10:3332–3337 (1994); Lenhard et al., J. Electroanal. Chem. 78:195–201 (1977), both of which are expressly incorporated by reference). When carbon based electrodes are used, $F_1$ may be an amino moiety (preferably a primary amine; see for example Deinhammer et al., Langmuir 10:1306–1313 (1994)). Thus, preferred $F_1$ moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the conductive oligomer may be attached to the electrode with more than one $F_1$ moiety; the $F_1$ moieties may be the same or different. Thus, for example, when the electrode is a gold electrode, and $F_1$ is a sulfur atom or moiety, multiple sulfur atoms may be used to attach the conductive oligomer to the electrode. Preferably, the $F_1$ moiety is just a sulfur atom, but substituted sulfur moieties may also be used.

In a preferred embodiment, the electrode is a gold electrode, and attachment is via a sulfur linkage as is well known in the art, i.e. the $F_1$ moiety is a sulfur atom or moiety. Although the exact characteristics of the gold-sulfur attachment are not known, this linkage is considered covalent for the purposes of this invention.

In a preferred embodiment, the electrode is a carbon electrode, i.e. a glassy carbon electrode, and attachment is via a nitrogen of an amine group.

In general, one of two general schemes may be followed to synthesize the compositions of the invention. In a preferred embodiment, the spacer is synthesized and the redox active complex, comprising the redox active molecule and the binding ligand is also made separately. These two are added together, and then added to the electrode. Alternatively, in a preferred embodiment, the spacer is made and attached to the electrode. The redox active complex is made, and then it is added to the spacer. General synthetic schemes may be found in PCT US97/20014.

Thus, in a preferred embodiment, electrodes are made that comprise conductive oligomers attached to redox active moieties and/or binding ligands for the purposes of analyte assays, as is more fully described herein. As will be appreciated by those in the art, electrodes can be made that have a single species of binding ligand (i.e. specific for a particular analyte) or multiple binding ligand species (i.e. multiple analytes).

In addition, as outlined herein, the use of a solid support such as an electrode enables the use of these binding ligands in an array form. The use of arrays of binding ligands specific for oligonucleotides are well known in the art. In addition, techniques are known for "addressing" locations within an electrode and for the surface modification of electrodes.

Thus, in a preferred embodiment, arrays of different binding ligands are laid down on the electrode, each of which are covalently attached to the electrode via a conductive linker. In this embodiment, the number of different species of binding ligands may vary widely, from one to thousands, with from about 4 to about 100,000 being preferred, and from about 10 to about 10,000 being particularly preferred.

In a preferred embodiment, the electrode further comprises a passivation agent, preferably in the form of a monolayer on the electrode surface. For some analytes, such as nucleic acids, the efficiency of analyte binding (i.e. hybridization) may increase when the binding ligand is at a distance from the electrode. In addition, the presence of a monolayer can decrease non-specific binding to the surface. A passivation agent layer facilitates the maintenance of the binding ligand and/or analyte away from the electrode surface. In addition, a passivation agent serves to keep charge carriers away from the surface of the electrode. Thus, this layer helps to prevent electrical contact between the electrodes and the electron transfer moieties, or between the electrode and charged species within the solvent. Such contact can result in a direct "short circuit" or an indirect short circuit via charged species which may be present in the sample. Accordingly, the monolayer of passivation agents is preferably tightly packed in a uniform layer on the electrode surface, such that a minimum of "holes" exist. Alternatively, the passivation agent may not be in the form of a monolayer, but may be present to help the packing of the conductive oligomers or other characteristics.

The passivation agents thus serve as a physical barrier to block solvent accesibility to the electrode. As such, the passivation agents themselves may in fact be either (1) conducting or (2) nonconducting, i.e. insulating, molecules.

Thus, in one embodiment, the passivation agents are conductive oligomers, as described herein, with or without a terminal group to block or decrease the transfer of charge to the electrode. Other passivation agents which may be conductive include oligomers of —$(CF_2)_n$—, —$(CHF)_n$— and —$(CFR)_n$—. In a preferred embodiment, the passivation agents are insulator moieties.

An "insulator" is a substantially nonconducting oligomer, preferably linear. By "substantially nonconducting" herein is meant that the rate of electron transfer through the insulator is slower than the rate of electron transfer through the a conductive oligomer. Stated differently, the electrical resistance of the insulator is higher than the electrical resistance of the conductive oligomer. It should be noted however that even oligomers generally considered to be insulators, such as —$(CH_2)_{16}$ molecules, still may transfer electrons, albeit at a slow rate.

In a preferred embodiment, the insulators have a conductivity, S, of about $10^{-7}$ $\Omega^{-1}cm^{-1}$ or lower, with less than about $10^{-8}$ $\Omega^{-1}cm^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

The passivation agents, including insulators, may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. In addition, the terminus of the passivation agent, including insulators, may contain an additional group to influence the exposed surface of the monolayer. For example, the addition of charged, neutral or hydrophobic groups may be done to inhibit non-specific binding from the sample, or to influence the kinetics of binding of the analyte, etc. For example, there may be negatively charged groups on the terminus to form a charged surface such that when the nucleic acid is DNA or RNA the nucleic acid is repelled or prevented from lying down on the surface.

The length of the passivation agent will vary as needed. Generally, the length of the passivation agents is similar to the length of the conductive oligomers, as outlined above. In addition, the conductive oligomers may be basically the same length as the passivation agents or longer than them, resulting in the binding ligands being more accessible to the solvent.

The monolayer may comprise a single type of passivation agent, including insulators, or different types. Suitable insulators are known in the art, and include, but are not limited to, —$(CH_2)_n$—, —$(CRH)_n$—, and —$(CR_2)_n$—, ethylene glycol or derivatives using other heteroatoms in place of oxygen, i.e. nitrogen or sulfur (sulfur derivatives are not preferred when the electrode is gold).

The passivation agents are generally attached to the electrode in the same manner as the conductive oligomer, and may use the same "$F_1$" linker as defined above.

The target analyte, contained within a test sample, is added to the electrode containing either a solvent accessible redox active complex or a mixture of solvent accessible transition metal complexes and binding ligands, under conditions that if present, the target analyte will bind to the binding ligand. These conditions are generally physiological conditions. Generally a plurality of assay mixtures are run in parallel with different concentrations to obtain a differential response to the various concentrations. Typically, one of these concentrations serves as a negative control, i.e., at zero concentration or below the level of detection. In addition, any variety of other reagents may be included in the screening assay. These include reagents like salts, neutral proteins, e.g. albumin, detergents, etc which may be used to facilitate optimal binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In a preferred embodiment, the target analyte will bind the binding ligand reversibly, i.e. non-covalently, such as in protein-protein interactions of antigens-antibodies, enzyme-substrate (or some inhibitors) or receptor-ligand interactions.

In a preferred embodiment, the target analyte will bind the binding ligand irreversibly, for example covalently. For example, some enzyme-inhibitor interactions are considered irreversible. Alternatively, the analyte initially binds reversibly, with subsequent manipulation of the system which results in covalent attachment. For example, chemical cross-linking after binding may be done, as will be appreciated by those in the art. For example, peptides may be cross-linked using a variety of bifunctional agents, such as maleimidobenzoic acid, methyidithioacetic acid, mercaptobenzoic acid, S-pyridyl dithiopropionate, etc. Alternatively, functionally reactive groups on the target analyte and the binding ligand may be induced to form covalent attachments.

Upon binding of the analyte to the binding moiety, the solvent accessible transition metal complex becomes solvent inhibited. By "solvent inhibited transition metal complex" herein is meant the solvent reorganization energy of the solvent inhibited transition metal complex is less than the solvent reorganization energy of the solvent accessible transition metal complex. As noted above, this may occur in several ways. In a preferred embodiment, the target analyte provides a coordination atom, such that the solvent accessible transition metal complex loses at least one, and preferably several, of its small polar ligands. Alternatively, in a preferred embodiment, the proximity of the target analyte to the transition metal complex does not result in ligand exchange, but rather excludes solvent from the area surrounding the metal ion (i.e. the first or second coordination sphere) thus effectively lowering the required solvent reorganization energy.

In a preferred embodiment, the required solvent reorganization energy decreases sufficiently to result in a decrease in the $E_0$ of the redox active molecule by at about 100 mV, with at least about 200 mV being preferred, and at least about 300–500 mV being particularly preferred.

In a preferred embodiment, the required solvent reorganization energy decreases by at least 100 mV, with at least about 200 mV being preferred, and at least about 300–500 mV being particularly preferred.

In a preferred embodiment, the the required solvent reorganization energy decreases sufficiently to result in a rate change of electron transfer ($k_{ET}$) between the solvent inhibited transition metal complex and the electrode relative to the rate of electron transfer between the solvent accessible transition metal complex and the electrode. In a preferred embodiment, this rate change is greater than about a factor of 3, with at least about a factor of 10 being preferred and at least about a factor of 100 or more being particularly preferred.

The determination of solvent reorganization energy will be done as is appreciated by those in the art.

Briefly, as outlined in Marcus theory, the electron transfer rates ($k_{ET}$) are determined at a number of different driving forces (or free energy, $-\Delta G°$); the point at which the rate equals the free energy is the activationless rate ($\lambda$). This may be treated in most cases as the equivalent of the solvent reorganization energy; see Gray et al. Ann. Rev. Biochem. 65:537 (1996), hereby incorporated by reference.

The solvent inhibited transition metal complex, indicating the presence of a target analyte, is detected by intiating electron transfer and detecting a signal characteristic of electron transfer between the solvent inhibited redox active molecule and the electrode.

Electron transfer is generally initiated electronically, with voltage being preferred. A potential is applied to a sample containing modified nucleic acid probes. Precise control and variations in the applied potential can be via a potentiostat and either a three electrode system (one reference, one sample and one counter electrode) or a two electrode system (one sample and one counter electrode). This allows matching of applied potential to peak electron transfer potential of the system which depends in part on the choice of transition metal complexes and in part on the conductive oligomer used.

Preferably, initiation and detection is chosen to maximize the relative difference between the solvent reorganization energies of the solvent accessible and solvent inhibited transition metal complexes.

Electron transfer between the transition metal complex and the electrode can be detected in a variety of ways, with electronic detection, including, but not limited to, amperommetry, voltammetry, capacitance and impedance being preferred. These methods include time or frequency dependent methods based on AC or DC currents, pulsed methods, lock-in techniques, and filtering (high pass, low pass, band pass). In some embodiments, all that is required is electron transfer detection; in others, the rate of electron transfer may be determined.

In a preferred embodiment, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry, and photoelectrochemistry.

In a preferred embodiment, monitoring electron transfer is via amperometric detection. This method of detection involves applying a potential (as compared to a separate reference electrode) between the electrode containing the compositions of the invention and an auxiliary (counter) electrode in the test sample. Electron transfer of differing efficiencies is induced in samples in the presence or absence of target analyte.

The device for measuring electron transfer amperometrically involves sensitive current detection and includes a means of controlling the voltage potential, usually a potentiostat. This voltage is optimized with reference to the potential of the redox active molecule.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the redox active molecules and the electrode. In addition, other properties of insulators (such as resistance) and of conductors (such as conductivity, impedance and capicitance) could be used to monitor electron transfer between the redox active molecules and the electrode. Finally, any system that generates a current (such as electron transfer) also generates a small magnetic field, which may be monitored in some embodiments.

In a preferred embodiment, the system may be calibrated to determine the amount of solvent accessible transition metal complexes on an electrode by running the system in organic solvent prior to the addition of target. This is quite significant to serve as an internal control of the sensor or system. This allows a preliminary measurement, prior to the addition of target, on the same molecules that will be used for detection, rather than rely on a similar but different control system. Thus, the actual molecules that will be used for the detection can be quantified prior to any experiment. Running the system in the absence of water, i.e. in organic solvent such as acetonitrile, will exclude the water and substantially negate any solvent reorganization effects. This will allow a quantification of the actual number of molecules that are on the surface of the electrode. The sample can then be added, an output signal determined, and the ratio of bound/unbound molecules determined. This is a significant advantage over prior methods.

It should be understood that one benefit of the fast rates of electron transfer observed in the compositions of the invention is that time resolution can greatly enhance the signal-to-noise results of monitors based on electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, orders of magnitude improvements in signal-to-noise may be achieved.

Without being bound by theory, it appears that target analytes, bound to an electrode, may respond in a manner similar to a resistor and capacitor in series. Also, the $E_0$ of the redox active molecule can shift as a result of the target analyte binding. Furthermore, it may be possible to distinguish between solvent accessible and solvent inhibited transition metal complexes on the basis of the rate of electron transfer, which in turn can be exploited in a number of ways for detection of the target analyte. Thus, as will be appreciated by those in the art, any number of initiation-detection systems can be used in the present invention.

In a preferred embodiment, electron transfer is initiated and detected using direct current (DC) techniques. As noted above, the $E_0$ of the redox active molecule can shift as a result of the change in the solvent reorganization energy upon target analyte binding. Thus, measurements taken at the $E_0$ of the solvent accessible transition metal complex and at the $E_0$ of the solvent inhibited complex will allow the detection of the analyte. As will be appreciated by those in the art, a number of suitable methods may be used to detect the electron transfer.

In a preferred embodiment, electron transfer is initiated using alternating current (AC) methods. A first input electrical signal is applied to the system, preferably via at least the sample electrode (containing the complexes of the invention) and the counter electrode, to initiate electron transfer between the electrode and the second electron transfer moiety. Three electrode systems may also be used, with the voltage applied to the reference and working electrodes. In this embodiment, the first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 10 MHz, with from about 1 Hz to about 1 MHz being preferred, and from about 1 Hz to about 100 kHz being especially preferred.

In a preferred embodiment, the first input signal comprises a DC component and an AC component. That is, a DC offset voltage between the sample and counter electrodes is swept through the electrochemical potential of the electron transfer moiety. The sweep is used to identify the DC voltage at which the maximum response of the system is seen. This is generally at or about the electrochemical potential of the transition metal complex. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. On top of the DC offset voltage, an AC signal component of variable amplitude and frequency is applied. If the transition metal complex has a low enough solvent reorganization energy to respond to the AC perturbation, an AC current will be produced due to electron transfer between the electrode and the transition metal complex.

In a preferred embodiment, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, as noted above, it may be possible to distinguish between solvent accessible and solvent inhibited transition metal complexes on the basis of the rate of electron transfer, which in turn can be used either to distinguish the two on the basis of frequency or overpotential.

In a preferred embodiment, measurements of the system are taken at at least two separate amplitudes or overpotentials, with measurements at a plurality of amplitudes being preferred. As noted above, changes in response as a result of changes in amplitude may form the basis of identification, calibration and quantification of the system.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the transition metal complexes, higher frequencies result in a loss or decrease of output signal. At some point, the frequency will be greater than the rate of electron transfer through even solvent inhibited transition metal complexes, and then the output signal will also drop.

In addition, the use of AC techniques allows the significant reduction of background signals at any single frequency due to entities other than the target analyte, i.e. "locking out" or "filtering" unwanted signals. That is, the frequency response of a charge carrier or redox active species in solution will be limited by its diffusion coefficient. Accordingly, at high frequencies, a charge carrier may not diffuse rapidly enough to transfer its charge to the electrode, and/or the charge transfer kinetics may not be fast enough. This is particularly significant in embodiments that do not utilize a passivation layer monolayer or have partial or insufficient monolayers, i.e. where the solvent is accessible to the electrode. As outlined above, in DC techniques, the presence of "holes" where the electrode is accessible to the solvent can result in solvent charge carriers "short circuiting" the system. However, using the present AC techniques, one or more frequencies can be chosen that prevent a frequency response of one or more charge carriers in solution, whether or not a monolayer is present. This is particularly significant since many biological fluids such as blood contain significant amounts of redox active species which can interfere with amperometric detection methods.

In a preferred embodiment, measurements of the system are taken at at least two separate frequencies, with measurements at a plurality of frequencies being preferred. A plurality of frequencies includes a scan. In a preferred embodiment, the frequency response is determined at at least two, preferably at least about five, and more preferably at least about ten frequencies.

After transmitting the input signal to initiate electron transfer, an output signal is received or detected. The presence and magnitude of the output signal will depend on the overpotential/amplitude of the input signal; the frequency of the input AC signal; the composition of the intervening medium, i.e. the impedance, between the electron transfer moieties; the DC offset; the environment of the system; and the solvent. At a given input signal, the presence and magnitude of the output signal will depend in general on the solvent reorganization energy required to bring about a change in the oxidation state of the metal ion. Thus, upon transmitting the input signal, comprising an AC component and a DC offset, electrons are transferred between the electrode and the transition metal complex, when the solvent reorganization energy is low enough, the frequency is in range, and the amplitude is sufficient, resulting in an output signal.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

In addition, those in the art will appreciate that it is also possible to use the compositions of the invention in assays that rely on a loss of signal. For example, a first measurement is taken when the transition metal complex is inhibited, and then the system is changed as a result of the introduction of a target analyte, causing the solvent inhibited molecule to become solvent accessible, resulting in a loss of signal. This may be done in several ways, as will be appreciated by those in the art.

In a preferred embodiment, a first measurement is taken when the target analyte is present. The target analyte is then removed, for example by the use of high salt concentrations or thermal conditions, and then a second measurement is taken. The quantification of the loss of the signal can serve as the basis of the assay.

Alternatively, the target analyte may be an enzyme. In this preferred embodiment, the transition metal complex is made solvent inhibited by the presence of an enzyme substrate or analog, preferably, but not required to be covalently attached to the transition metal complex, preferably as one or more ligands. Upon introduction of the target enzyme, the enzyme associates with the substrate to cleave or otherwise sterically alter the substrate such that the transition metal complex is made solvent accessible. This change can then be detected. This embodiment is advantageous in that it results in an amplification of the signal, since a single enzyme molecule can result in multiple solvent accessible molecules. This may find particular use in the detection of bacteria or other pathogens that secrete enzymes, particularly scavenger proteases or carbohydrases.

Similarly, a preferred embodiment utilizes competition-type assays. In this embodiment, the binding ligand is the same as the actual molecule for which detection is desired; that is, the binding ligand is actually the target analyte or an analog. A binding partner of the binding ligand is added to the surface, such that the transition metal complex becomes solvent inhibited, electron transfer occurs and a signal is generated. Then the actual test sample, containing the same or similar target analyte which is bound to the electrode, is added. The test sample analyte will compete for the binding partner, causing the loss of the binding partner on the surface and a resulting decrease in the signal.

A similar embodiment utilizes a target analyte (or analog) is covalently attached to a preferably larger moiety (a "blocking moiety"). The analyte-blocking moiety complex is bound to a binding ligand that binds the target analyte, serving to render the transition metal complex solvent inhibited. The introduction of the test sample target analyte serves to compete for the analyte-blocking moiety complex, releasing the larger complex and resulting in a more solvent accessible molecule.

In addition, while the majority of the above discussion is directed to the use of the invention when the compositions are attached to surfaces such as electrodes, those of skill in the art will appreciate that solution-based systems are also possible. In this embodiment, solvent accessible transition metal complexes are attached to binding ligands (either directly or using short linkers that keep the binding ligand and the transition metal complex in close enough proximity to allow detection) to form soluble redox active complexes. Upon binding of an analyte, the transition metal complex becomes solvent inhibited, and a change in the system can be detected. In a preferred embodiment, the reaction is monitored by fluorescence or electrochemical means. Alternatively, the reaction may be monitored electronically, using mediators.

The present invention further provides apparatus for the detection of analytes using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In a preferred embodiment, the first measuring electrode comprises a redox active complex, covalently attached via a spacer, and preferably via a conductive oligomer, such as are described herein. Alternatively, the first measuring electrode comprises covalently attached transition metal complexes and binding ligands.

The apparatus further comprises a voltage source electrically connected to the test chamber; that is, to the measuring electrodes. Preferably, the voltage source is capable of delivering AC and DC voltages, if needed.

In a preferred embodiment, the apparatus further comprises a processor capable of comparing the input signal and the output signal. The processor is coupled to the electrodes and configured to receive an output signal, and thus detect the presence of the target analyte.

The compositions of the present invention may be used in a variety of research, clinical, quality control, or field testing settings.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entireity.

EXAMPLE

Preparation of Solvent Accessible Redox Active Moiety

In this example, a solution based sensor was made, using a redox active complex comprising a ruthenium complex and a biotin binding ligand. A transition metal complex of ruthenium, with small polar coordination ligands ($NH_3$), was made. One of the coordination atoms was provided by the binding ligand norbiotin (biotin conjugated with a primary amine via four carbon linker), such that upon binding of avidin, the transition metal complex goes from solvent accessible to solvent inhibited. This was detected fluorometrically. Alternatively, the redox active complex of ruthenium and biotin can be activated and added to a surface to form an electrode-based sensor.

The synthesis of [trans RuIII $(NH_3)_4$(norbiotin) Cl]$C_{12}$ was carried in several steps. The first intermediate in the reaction sequence is trans-[$SO_2(NH_3)$ RuIICl]Cl] and was synthesized in the following manner.

2.5 gr. (8.5mmoles) of [$(NH_3)_5$RuIIICl]$Cl_2$ was slurried in 65 ml of pre-heated water (−70° C.) in a three neck round bottom flask equipped with a thermometer, reflux condenser and gas inlet. To this flask was added 3.55gr (2.4 mmoles) of $NaHSO_3$ and immediately a continuous stream of SO gas was bubbled through the solution and the mixture allowed to warm to 83° C. The reaction was allowed to proceed for 90 minutes. The solution was cooled to 0° C., and the product collected and washed several times with acetone.

The solid was slurried in 200 mls of 6M HCl and heated to a vigorous reflux for 20min in a 500 ml flask. The reaction mixture was filtered and allowed to stand at 4° C. overnight. The rust colored crystals of trans-[$SO(NH_3)$ RuIICl]Cl were collected and slurried in 50 ml of water, heated to 40° C., an excess of norbiotin was added and the solution allowed to react for 30 minutes. The solution was transferred to a 1000 ml flask and 750 ml of acetone was added and allowed to stir for 10 minutes. The solid was collected, washed with acetone and dried in vacuo.

The solid was dissolved in a minimum of water and filtered. To this solution was added dropwise with stirring a 50:50 mixture of 30% $H_2O_2$ and 2N HCl. A solid was obtained by the addition of 15 volumes of acetone, collected and dried in vacuo. This product was dissolved in a minimum amount of degassed 0.15N HCl and thoroughly degassed. Zinc-Hg amalgam was prepared, the solution was transferred to the zinc amalgam, and the reaction allowed to proceed for 1 hour. A previously degassed solution of 1 M $BaCl_2$ was added.

The solid, including the amalgam, was filtered as quickly as possible into a filter flask containing 3–4ml of 30% $H_2O_2$ and 3M HCl. The product was obtained from the yellow solution via precipitation using 15 volumes of acetone, collected, washed and dried in vacuo. The solid was redissolved in a minimum amount of 0.01N HCl and applied to a 4×30 cm column of SP Sephadex C-25. The product was recovered using 0.2N HCl.

The collected fractions were evaporated to dryness, dissolved in a minimum amount of 0.01N HCl, filtered and precipitated with 15 volumes of acetone. The product [trans RuIII$(NH_3)_4$(norbiotin) Cl]$Cl_2$ was collected, and dried in vacuo.

For a solution-based sensor, the material was taken up in water and a fluorescence measurement was taken; the sample exhibited no fluorescence; that is, the presence of water was a barrier to fluorescence. Avidin was added and a second fluorescence measurement was taken; in the presence of avidin, fluorescence was detected. This shows that the environment around the complex is altered such that the water is no longer a barrier to fluorescence; i.e. fluorescence is not quenched.

For an electrode-based sensor, the material can be activated for addition to a conductive oligomer as follows. The [trans RuIII$(NH_3)_4$(norbiotin) Cl]$Cl_2$ is activated by reduction of the complex using Zinc-Hg amalgam to form [trans RuII$(NH_3)_4$(norbiotin) $H_2O$]$Cl_2$ under inert atmosphere conditions. To this material is added a conductive oligomer that terminates in a group suitable to serve as a coordination atom, such as a nitrogen-containing species, such as analine. The conductive oligomer containing the redox active complex (i.e. the solvent accessible transition metal complex and the binding ligand) can then be mixed with other monolayer-forming components such as passivation agents and added to the electrode using known techniques, such as those described in PCT US97/20014, hereby incorporated by reference.

I claim:

1. A composition comprising an electrode comprising a covalently attached binding ligand that will bind a target analyte and a covalently attached solvent accessible transition metal complex comprising a metal selected from the group consisting of manganese, technetium, rhenium, iron, ruthenium, osmium, cobalt, rhodium, iridium, nickel, palladium, platinum, copper, silver and gold, such that upon binding of said target analyte, a solvent inhibited transition metal complex is formed.

2. A composition according to claim 1 wherein said solvent accessible transition metal complex has at least two coordination sites occupied by polar coordination groups.

3. A composition according to claim 1 wherein said solvent accessible transition metal complex has at least one coordination site occupied by a water molecule.

4. A composition according to claim 1 wherein said electrode further comprises a self-assembled monolayer.

5. A composition according to claim 1 wherein said solvent accessible transition metal complex is covalently attached to said electrode via a conductive oligomer.

6. A composition according to claim 1 wherein said solvent accessible transition metal complex is linked to said binding ligand to form a redox active complex.

7. A composition according to claim 1 wherein said binding ligand is covalently attached to said electrode via a conductive oligomer.

8. An apparatus for the detection of target analytes in a test sample, comprising:
   a) a test chamber comprising a first and a second measuring electrode, wherein said first measuring electrode comprises:
      i) a covalently attached solvent accessible transition metal comprising a metal selected from the group consisting of manganese, technetium, rhenium, iron, ruthenium, osmium, cobalt, rhodium, iridium, nickel, palladium, platinum, copper, silver and gold; and
      ii) a covalently attached binding ligand that will bind said target analyte;
   such that upon binding of said target analyte a solvent inhibited transition metal complex is formed;
   b) an AC/DC voltage source electrically connected to said test chamber.

9. An apparatus according to claim 8 wherein said covalent attachment is via a spacer.

10. An apparatus according to claim 8 further comprising a processor coupled to said AC/DC voltage source.

11. An apparatus according to claim 8 wherein said electrode further comprises a self-assembled monolayer.

12. A composition according to claim 1 wherein said binding ligand will bind a protein.

13. A composition according to claim 1 wherein said binding ligand will bind a nucleic acid.

14. A composition according to claim 1 wherein said binding ligand is a protein.

15. An apparatus according to claim 9 wherein said spacer is a conductive oligomer.

16. A composition according to claim 1 wherein said solvent accessible transition metal complex is attached to said binding ligand.

17. A composition according to claim 5 or 7 wherein said conductive oligomer has the formula,

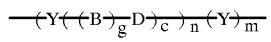

wherein Y is an aromatic group;
n is an integer from 1 to 50;
g is either 1 or zero,
e is an integer from zero to 10; and
m is zero or 1;
wherein when g is 1, B—D is a conjugated bond; and
wherein when g is zero, e is 1 and D is preferably carbonyl, or a heteroatom moiety, wherein the heteroatom is selected from the group consisting of oxygen, sulfur, nitrogen and phosphorus.

18. A composition according to claim 17 wherein said aromatic group is phenyl, g is 1, and B—D is an acetylene linkage.

19. A composition according to claim 5 or 7 wherein said conductive oligomer has the formula:

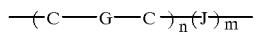

wherein
n is an integer from 1 to 50;
m is zero or 1;
C is carbon;
J is carbonyl or a heteroatom moiety, wherein the heteroatom is selected from the group consisting of oxygen, nitrogen, silicon, phosphorus and sulfur; and
G is bond selected from alkane, alkene or acetylene.

20. A composition according to claim 1 wherein said metal is ruthenium.

21. A composition according to claim 1 wherein said metal is osmium.

22. A composition according to claim 1 wherein said metal is iron.

23. A composition according to claim 1 wherein said metal is platinum.

24. A composition according to claim 1 wherein said metal is palladium.

25. A composition according to claim 1 wherein said metal is manganese.

26. A composition according to claim 1 wherein said metal is technetium.

27. A composition according to claim 1 wherein said metal is rhenium.

28. A composition according to claim 1 wherein said metal is cobalt.

29. A composition according to claim 1 wherein said metal is rhodium.

30. A composition according to claim 1 wherein said metal is iridium.

31. A composition according to claim 1 wherein said metal is nickel.

32. A composition according to claim 1 wherein said metal is copper.

33. A composition according to claim 1 wherein said metal is silver.

34. A composition according to claim 1 wherein said metal is gold.

35. An apparatus according to claim 8 wherein said solvent accessible transition metal complex attached to said binding ligand.

36. An apparatus according to claim 15 therein said conductive oligomer has the formula:

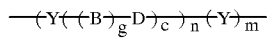

wherein Y is an aromatic group;
n is an integer from 1 to 50;
g is either 1 or zero;
e is an integer from zero to 10; and
m is zero or 1;
wherein when g is 1, B—D is a conjugated bond; and
wherein when g is zero, e is 1 and D is preferably carbonyl, or a heteroatom moiety, wherein the heteroatom is selected from the group consisting of oxygen, sulfur, nitrogen and phosphorus.

37. An apparatus according to claim 36 wherein said aromatic group is phenyl, g is 1, and B—D is an acetylene linkage.

38. An apparatus according to claim 15 wherein said conductive oligomer has the formula.

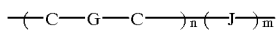

Structure 4 wherein
   n is an integer from 1 to 50;
   m is zero or 1;
   C is carbon,
   J is carbonyl or a heteroatom moiety, wherein the heteroatom is selected from the group consisting of oxygen, nitrogen, silicon, phosphorus and sulfur; and
   G is bond selected from alkane, alkene or acetylene.

39. An apparatus according to claim 8 wherein said metal is ruthenium.

40. An apparatus according to claim 8 wherein said metal is osmium.

41. An apparatus according to claim 8 wherein said metal is iron.

42. An apparatus according to claim 8 wherein said metal is platinum.

43. An apparatus according to claim 8 wherein said metal is palladium.

44. An apparatus according to claim 8 wherein said metal is manganese.

45. An apparatus according to claim 8 wherein said metal is technetium.

46. An apparatus according to claim 8 wherein said metal is rhenium.

47. An apparatus according to claim 8 wherein said metal is cobalt.

48. An apparatus according to claim 8 wherein said metal is rhodium.

49. An apparatus according to claim 8 wherein said metal is iridium.

50. An apparatus according to claim 8 wherein said metal is nickel.

51. An apparatus according to claim 8 wherein said metal is copper.

52. An apparatus according to claim 8 wherein said metal is silver.

53. An apparatus according to claim 8 wherein said metal is gold.

54. An apparatus according to claim 8 wherein said solvent accessible transition metal complex has at least one coordination site occupied by a polar coordination group.

55. An apparatus according to claim 8 wherein said solvent accessible transition metal complex has at least one coordination site occupied by a water molecule.

56. An apparatus according to claim 8 wherein said solvent accessible transition metal complex has at least one coordination site occupied by a water molecule.

57. A composition according to claim 1 wherein said solvent accessible transition metal complex has a solvent reorganization energy of greater than about 1000 meV.

58. A composition according to claim 1 wherein said solvent accessible transition metal complex has a solvent reorganization energy of greater than about 500 meV.

59. A composition according to claim 1 wherein the solvent reorganization energy of said solvent accessible transition metal complex decreases by at least 100 meV upon binding of said analyte to form said solvent inhibited transition metal complex.

60. A composition according to claim 1 wherein the solvent reorganization energy of said solvent accessible transition metal complex decreases to result in a decrease in the $E_0$ by at least 100 meV upon binding of said analyte to form said solvent inhibited transition metal complex.

61. An apparatus according to claim 8 wherein said solvent accessible transition metal complex has a solvent reorganization energy of greater than about 1000 meV.

62. An apparatus according to claim 8 wherein said solvent accessible transition metal complex has a solvent reorganization energy of greater than about 500 meV.

63. An apparatus according to claim 8 wherein the solvent reorganization energy of said solvent accessible transition metal complex decreases by at least 100 meV upon binding of said analyte to form said solvent inhibited transition metal complex.

64. An apparatus according to claim 8 wherein the solvent reorganization energy of said solvent accessible transition metal complex decreases to result in a decrease in the $E_0$ by at least 100 meV upon binding of said analyte to form said solvent inhibited transition metal complex.

* * * * *